United States Patent

Py

[11] Patent Number: 5,685,869
[45] Date of Patent: Nov. 11, 1997

[54] APPARATUS FOR APPLYING MEDICAMENT TO AN EYE

[75] Inventor: Daniel Py, 8 Normandy Rd., Larchmont, N.Y. 10538

[73] Assignee: Daniel Py, Larchmont, N.Y.

[21] Appl. No.: 433,856

[22] Filed: May 2, 1995

Related U.S. Application Data

[62] Division of Ser. No. 209,957, Mar. 11, 1994, Pat. No. 5,613,957, which is a continuation of Ser. No. 801,243, Dec. 2, 1991, abandoned.

[51] Int. Cl.$^6$ .............................. A61M 35/00; B67D 5/64
[52] U.S. Cl. .......................... 604/294; 604/295; 604/298; 222/340; 222/422; 222/494
[58] Field of Search ...................... 604/294–300; 222/340, 387, 494, 420, 421; 417/552

[56] References Cited

U.S. PATENT DOCUMENTS

| | | |
|---|---|---|
| Re. 33,801 | 1/1992 | Green . |
| 2,117,296 | 5/1938 | Cahoon ................................. 221/147 |
| 2,281,051 | 4/1942 | Roger ................................... 221/148 |
| 2,778,360 | 1/1957 | Miskel ..................................... 604/87 |
| 3,162,217 | 12/1964 | Poli, Jr. et al. ......................... 141/27 |
| 3,187,960 | 6/1965 | Gorman ................................. 222/321 |
| 3,229,864 | 1/1966 | Roder .................................... 222/321 |
| 3,302,834 | 2/1967 | Alsop .................................... 222/162 |
| 3,411,503 | 11/1968 | Santomieri ............................... 604/87 |
| 3,488,002 | 1/1970 | Mina ...................................... 239/327 |
| 3,563,240 | 2/1971 | Silver .................................... 604/87 |
| 3,563,415 | 2/1971 | Ogle ..................................... 222/145 |
| 3,595,439 | 7/1971 | Newby et al. . |
| 3,684,136 | 8/1972 | Baumann ................................. 604/87 |
| 3,718,139 | 2/1973 | Hanford . |
| 3,731,853 | 5/1973 | Baumann et al. . |
| 3,739,947 | 6/1973 | Baumann et al. . |
| 3,741,439 | 6/1973 | Vehrs .................................... 222/103 |
| 3,756,390 | 9/1973 | Abbey et al. . |
| 3,993,064 | 11/1976 | McCarthy et al. .................. 128/218 A |
| 4,013,370 | 3/1977 | Gingras ................................. 401/175 |
| 4,179,051 | 12/1979 | Thomas .................................. 222/494 |
| 4,220,264 | 9/1980 | Gamadia ................................. 222/207 |
| 4,273,290 | 6/1981 | Quinn .................................... 239/493 |
| 4,296,071 | 10/1981 | Weiss et al. . |
| 4,433,797 | 2/1984 | Galia ..................................... 222/207 |
| 4,471,890 | 9/1984 | Dougherty .............................. 222/190 |
| 4,498,904 | 2/1985 | Turner et al. ........................... 604/211 |
| 4,516,969 | 5/1985 | Kinter . |
| 4,529,511 | 7/1985 | Breeden et al. .......................... 210/94 |
| 4,531,944 | 7/1985 | Bechtle ................................. 604/302 |
| 4,623,337 | 11/1986 | Maurice ................................ 604/298 |
| 4,634,023 | 1/1987 | Tanaka et al. .......................... 222/105 |
| 4,639,248 | 1/1987 | Schweblin ............................. 604/187 |
| 4,648,532 | 3/1987 | Green ..................................... 604/87 |
| 4,673,396 | 6/1987 | Urbaniak ............................... 604/187 |
| 4,694,977 | 9/1987 | Graf et al. ............................. 222/259 |
| 4,722,459 | 2/1988 | Goncalves .............................. 222/135 |
| 4,739,906 | 4/1988 | LoTurco ................................ 222/494 |
| 4,784,652 | 11/1988 | Wikström .............................. 604/295 |
| 4,792,334 | 12/1988 | Py ....................................... 604/301 |
| 4,908,024 | 3/1990 | Py ....................................... 604/300 |
| 4,927,062 | 5/1990 | Walsh ................................... 222/420 |
| 4,930,999 | 6/1990 | Brunet et al. .......................... 417/552 |
| 4,944,430 | 7/1990 | Graf et al. ............................. 222/259 |
| 4,946,452 | 8/1990 | Py ....................................... 604/301 |
| 4,950,237 | 8/1990 | Henault et al. .......................... 604/82 |
| 4,964,544 | 10/1990 | Hanna et al. ........................... 222/181 |

(List continued on next page.)

Primary Examiner—John G. Weiss
Assistant Examiner—David J. Cho
Attorney, Agent, or Firm—Kenyon & Kenyon

[57] ABSTRACT

An apparatus is used to apply medicament to an eye and stores the medicament in a medicament chamber. A nozzle is coupled in fluid communication with the medicament chamber and is formed by an outer nozzle portion and an inner nozzle portion received within the outer nozzle portion. A seam is formed by the interface of the inner nozzle portion and the outer nozzle portion and is normally in a closed position to prevent the passage of medicament through the nozzle. The seam opens in response to the flow of medicament of sufficient pressure into the seam to permit the passage of medicament through the nozzle for release into the eye.

27 Claims, 2 Drawing Sheets

U.S. PATENT DOCUMENTS

| | | | |
|---|---|---|---|
| 4,982,875 | 1/1991 | Pozzi et al. | 604/87 |
| 5,024,355 | 6/1991 | Jouillat et al. | 222/162 |
| 5,025,957 | 6/1991 | Ranalletta et al. | 222/189 |
| 5,038,965 | 8/1991 | Cater | 222/255 |
| 5,078,691 | 1/1992 | Hamacher | 604/183 |
| 5,085,651 | 2/1992 | Py | 604/294 |
| 5,154,325 | 10/1992 | Ryder et al. | 222/189 |
| 5,154,702 | 10/1992 | Foyil | 604/212 |
| 5,168,757 | 12/1992 | Rabenau et al. | 73/714 |
| 5,183,184 | 2/1993 | Ranalletta et al. | 222/189 |
| 5,190,190 | 3/1993 | Fudalla | 222/494 |
| 5,207,659 | 5/1993 | Pennaneac'h et al. | 604/298 |
| 5,238,153 | 8/1993 | Castillo et al. | 222/189 |
| 5,238,156 | 8/1993 | Andris | 222/207 |
| 5,255,826 | 10/1993 | Ranalletta et al. | 222/209 |

1

APPARATUS FOR APPLYING MEDICAMENT TO AN EYE

This application is a divisional application of Ser. No. 08/209,957, filed on Mar. 11, 1994, now U.S. Pat. No. 5,613,957 which was a continuation of Ser. No. 07/801,243 originally filed on Dec. 2, 1991, now abandoned.

FIELD OF THE INVENTION

The present invention relates to apparatus for dispensing fluid through a nozzle, such as ocular treatment apparatus for applying medicament or other substances to an eye.

BACKGROUND INFORMATION

There are various known devices for applying medicament to the eye. A typical eye-drop container has a flexible vial and a nozzle for releasing drops of medicament into the eye by squeezing the vial. If the user squeezes too hard, too much medicament can be released and, as a result, drip down the user's cheek. There is typically no means provided for accurately controlling the volume of each dose of medicament released into the eye. Also, if the tip of the nozzle becomes contaminated, there is typically no means provided for preventing the contaminated tip from contaminating the medicament within the vial, and thus possibly causing infection by use of the contaminated medicament. Because the medicament in such devices is typically exposed to air upon opening the nozzle, it is not desirable to use such devices to administer preservative-free formulations of medicament, other than by providing single-dose containers. The single-dose containers, however, are typically relatively expensive to package, particularly when used for prescription medications.

SUMMARY OF THE INVENTION

The present invention is directed to an apparatus for applying medicament to an eye, comprising a medicament chamber for holding medicament, and a nozzle coupled in fluid communication with the medicament chamber. The nozzle defines a seam which is normally in a closed position for preventing the passage of medicament through the nozzle and which opens in response to the flow of medicament of sufficient pressure to permit the passage of the medicament through the nozzle for release into the eye.

In one apparatus of the present invention, the nozzle includes an outer nozzle portion and an inner nozzle portion received within the outer nozzle portion, and the seam is defined by the interface of the inner and outer nozzle portions. The outer nozzle portion is preferably made of a more flexible material in comparison to the inner nozzle portion for facilitating the opening of the seam in response to the flow of medicament of sufficient pressure for release through the nozzle into the eye.

In one embodiment of the present invention, the apparatus further comprises a piston member for pressurizing medicament to flow through the seam of the nozzle for release into the eye. The piston member is seated within a piston cavity coupled in fluid communication with the nozzle and the medicament chamber, and the piston member is moveable within the piston cavity to push medicament within the piston cavity through the seam for release into the eye. The piston cavity is preferably dimensioned to release a predetermined volume of medicament into the eye.

In another embodiment of the present invention, the apparatus comprises an actuating member for pressurizing medicament to flow into the seam for release into the eye. The actuating member is preferably coupled to a shaft member and moveable along the shaft member to pressurize medicament to flow into the seam. The shaft member defines at least one channel coupled in fluid communication with the seam for directing the flow of pressurized medicament upon movement of the actuating member along the shaft member into the seam. An apparatus of the present invention further comprises a flange member coupled to the shaft member for directing the flow of medicament pressurized upon movement of the actuating member toward the seam.

An apparatus of the present invention further comprises a wall defining a cavity coupled in fluid communication with the medicament chamber for receiving the flange member upon movement of the actuating member along the shaft member toward the flange member. The medicament within the cavity is pressurized by movement of the actuating member and directed into the seam. The wall defines at least one aperture for coupling the cavity in fluid communication with the medicament chamber, and the medicament within the cavity is directed into the seam upon movement of the actuating member toward the flange member.

One advantage of the apparatus of the present invention is that once a dose of medicament is released, the seam of the nozzle closes, and thus substantially prevents medicament which may have been exposed to air or foreign particles from passing back through the nozzle and into the apparatus, which can contaminate the remainder of medicament in the apparatus. Thus, the apparatus of the present invention is particularly suitable for storing multiple-dose quantities of medicament, because it substantially prevents the remainder of the medicament from becoming contaminated once the apparatus is used. The apparatus of the present invention is also particularly suitable for use with preservative-free formulations of medicament or other substances which require that each time a dose of fluid is released, that the remainder of the fluid remain in a contaminant-free environment. The apparatus of the present invention is also particularly suitable for use with medicaments which should not be exposed to air because of an undesirable chemical reaction, for example, prior to use.

Another advantage of the apparatus of the present invention is that a substantially predetermined volume of medicament can be released into the eye each time the apparatus is actuated. Accordingly, the apparatus of the present invention should substantially facilitate patient compliance with treatment. Other advantages of the apparatus of the present invention will become apparent in view of the following detailed description and drawings.

DETAILED DESCRIPTION

Figure 1:
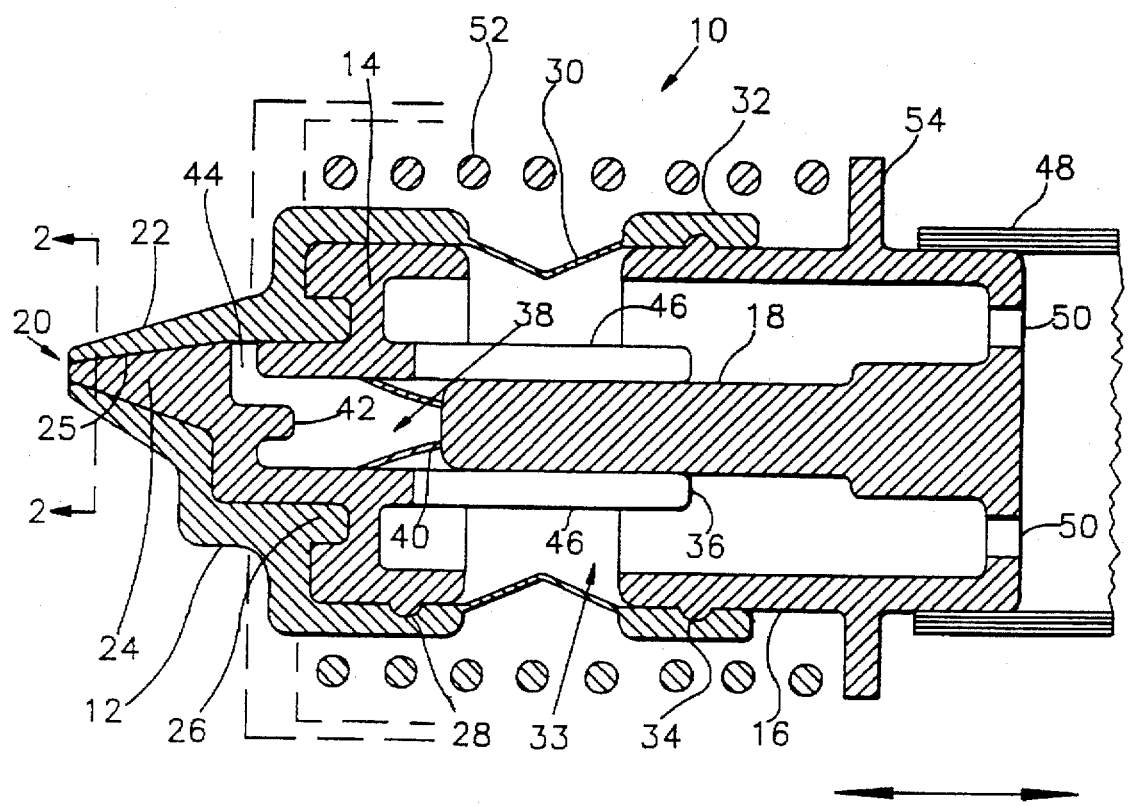
FIG. 1 is a cross-sectional view of an apparatus embodying the present invention.

In FIG. 1, an apparatus embodying the present invention is indicated generally by the reference numeral 10. The apparatus 10 includes an outer body 12, an inner body 14 fitted within the outer body 12, and a piston body 16 coupled to the outer body 12. The piston body 16 includes a piston 18 projecting into the inner body 12 substantially in the axial direction of the apparatus. The outer body 12 and inner body 14 define a nozzle 20 for releasing drops of medicament into a user's eye upon movement of the piston body 16, and thus the piston 18 relative to the outer body 12, as is described further below.

Figure 2:
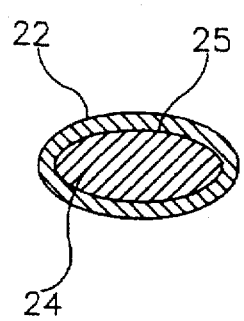
FIG. 2 is a cross-sectional view of the nozzle of the apparatus of FIG. 1 taken along the line 2—2 of FIG. 1.

The outer body 12 defines an outer nozzle portion 22 which receives an inner nozzle portion 24 of the inner body 14. As shown in FIGS. 1 and 2, a seam 25 is formed by the interface of the outer nozzle portion 22 and the inner nozzle portion 24 which is formed by the abutting surfaces of these two portions which taper inwardly toward the tip of the nozzle 20. The seam 25 is normally closed, but is opened when medicament of sufficient pressure is forced into the seam to release the medicament through the nozzle 20. The outer body 12 is preferably molded from a relatively flexible plastic material in comparison to the inner body 14. Thus, the outer nozzle portion 22 can be flexed relative to the inner nozzle portion 24 to permit the passage of medicament through the seam 25 and out of the nozzle 20, as is described further below. In the embodiment of the present invention illustrated, the outer body 12 is preferably made of a thermoelastic plastic, such as the plastic sold under the name KRATON® (a styrene-ethylene/butylene-styrene copolymer) by the Shell Company. The inner body 14 is preferably made of a more rigid plastic, such as the plastic sold under the name VALOX® (a polybutylene terephthalate engineering polyester) by the General Electric Company. These particular plastic materials are only exemplary, however, and other types of plastics can be used that are within the knowledge of those skilled in the art.

The outer body 12 includes an annular flange 26 which fits within a corresponding recess in the inner body 14, as shown in FIG. 1. The inner body 14, on the other hand, includes an annular lobe 28 which fits within a corresponding recess in the outer body 12. The inner body 14 is therefore pressed into the outer body 12 and coupled to the outer body by guiding the flange 26 and snapping the lobe 28 into the corresponding recesses.

The outer body 12 further includes a bellows 30 and a flange 32, which is in turn coupled to the piston body 16. A medicament chamber 33 is thus defined within the outer body 12 and the piston body 16, as shown in FIG. 1. The piston body 16 includes a lobe 34 which is snapped into a corresponding recess in the flange 32 to couple the piston body to the outer body 12, as shown in FIG. 1. The bellows 30 is adapted to flex inwardly to permit the piston body 16 and piston 18 to move relative to the outer and inner bodies 12 and 14, respectively, as indicated by the arrows in FIG. 1, to release medicament from the medicament chamber 33 through the nozzle 20.

The inner body 14 includes a substantially cylindrical wall 36 which projects toward the piston body 16 and slidably receives the piston 18, as shown in FIG. 1. The cylindrical wall 36 defines a drop cavity 38 located below the piston 18, which is adapted to hold a predetermined volume of medicament for release through the nozzle 20 into the eye. The drop cavity 38 is preferably dimensioned to hold less than 30 microliters of medicament, and for many medicaments, a quantity preferably within the range of 15 to 20 microliters. However, this capacity is purely exemplary, and can be changed as desired.

As shown in FIG. 1, the piston 16 includes a flexible rim 40 on its free end which is adapted to be maintained in sliding contact with the cylindrical wall 36. The inner body 14 further includes a knob 42 projecting from an interior surface toward the piston 18, and a channel 44 extending between the seam 25 and the drop cavity 38. The cylindrical wall 36 includes a pair of slots 46, each extending from the top of the drop cavity 38 to the free end of the cylindrical wall.

When the piston 18 is in the up position, i.e., the tip of the rim 40 is located above the base of each slot 46, medicament is permitted to flow from the medicament chamber 33 through the slots 46 and into the drop cavity 38. In FIG. 1, the piston 18 is shown in approximately the middle of its stroke. Then, on the downward stroke of the piston 18 (i.e., toward the nozzle 20), the medicament in the drop cavity 38 is forced through the channel 44 and into the seam 25. The pressurized medicament opens the seam 25 by causing the outer nozzle portion 22 to flex relative to the inner nozzle portion 24 to release the medicament into the eye. Then, once the medicament in the drop cavity 38 is released, the seam 25 returns to its normally closed state (i.e., the inner nozzle portion 24 is maintained in contact with the outer nozzle portion 22) to prevent air or foreign particles from passing through the nozzle and contaminating the remaining medicament within the apparatus.

The apparatus 10 further includes a medicament container 48 coupled on one end to the piston body 16 for holding medicament. The container 48 is preferably made of a plastic material and is sealed to the piston body 16 by welding, for example. The other end of the container 48 (not shown) is also sealed in a manner known to those skilled in the art. The piston body 16 includes several apertures 50 extending through its top wall to couple the container 48 in fluid communication with the medicament chamber 33. Medicament is therefore permitted to flow from the container 48, into the medicament chamber 33, and into the drop cavity 38 for release into the eye.

The apparatus 10 is preferably mounted within an ocular treatment apparatus substantially the same as the apparatus shown and described in U.S. Pat. No. 4,981,479, dated Jan. 1, 1991, which is assigned to the same assignee as the present invention, and is hereby expressly incorporated by reference as part of the present disclosure. The apparatus 10 is mounted within an ocular treatment apparatus as shown in U.S. Pat. No. 4,981,479 in place of the ocular vial shown in that patent. Additional modifications that are necessary in order to use the apparatus 10 with such an ocular treatment apparatus will be known to those skilled in the pertinent art, particularly in view of the teachings of U.S. Pat. No. 4,981,479. The outer body 12 is seated against a surface of the ocular treatment apparatus, as indicated in phantom lines in FIG. 1, in order to be maintained in a stationary position. A coil spring 52 is preferably seated between a surface of the ocular treatment apparatus and an annular flange 54 on the piston body 16, as also shown in FIG. 1. The coil spring 52 is provided to drive the piston body 16 to return to its normal position upon releasing medicament, as is described further below.

In the operation of the apparatus of the present invention, when the piston body 16 is located in the up position, medicament is permitted to flow from the medicament chamber 33, through the slots 46, and into the drop cavity 38 to fill the drop cavity. Then, when the piston body 16 is pushed toward the outer body 12 and into the down position, the downward stroke of the piston 18 forces the medicament in the drop cavity 38 through the channel 44 and into the seam 25.

On the downward stroke of the piston 18, the flexible rim 40 is forced outwardly into contact with the cylindrical wall 36, thus preventing the passage of medicament in the drop cavity 38 back into the medicament chamber 33. The pressurized medicament flowing through the channel 44 opens the seam 25 by forcing the flexible outer nozzle portion 22 away from the inner nozzle portion 24 to open the nozzle and release the medicament. Then, once the medicament is released, the outer nozzle portion 22 returns to its normal position in contact with the inner nozzle portion 24 so as to close the seam 25, and thus prevents the passage of medicament (which may be exposed to air or foreign particles) through the nozzle 20 and back into the drop cavity 38, which might otherwise contaminate the remaining medicament in the apparatus. The coil spring 52 then drives the piston body 16 and piston 18 back toward the up position causing a suction to develop within the drop cavity 38. Then, when the piston 18 reaches the up position, the suction facilitates the flow of medicament in the medicament chamber 33 into the drop cavity 38 and the apparatus 10 is ready to release another dose of medicament.

As will be recognized by those skilled in the art, one advantage of the apparatus of the present invention is that the nozzle 20 prevents the passage of medicament which has been exposed to air or foreign particles from entering the apparatus, and thus substantially prevents contamination of the medicament remaining within the apparatus. Another advantage of the apparatus 10 is that the pumping mechanism, which includes the piston 18, the cylindrical wall 36, and the drop cavity 38, is entirely enclosed within the contaminant-free environment of the medicament chamber 33. These advantages are particularly beneficial when using the apparatus to dispense preservative-free formulations of medicaments or other substances which cannot be exposed to air or foreign matter prior to use.

Figure 3:
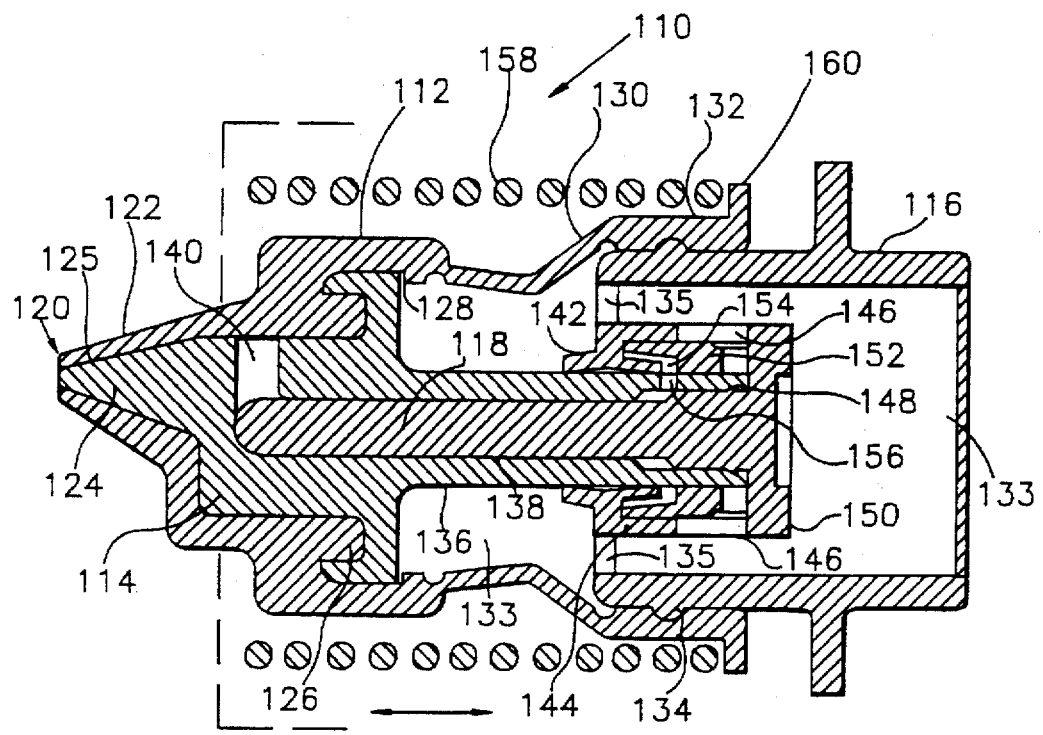
FIG. 3 is a cross-sectional view of another apparatus embodying the present invention.
Figure 4:
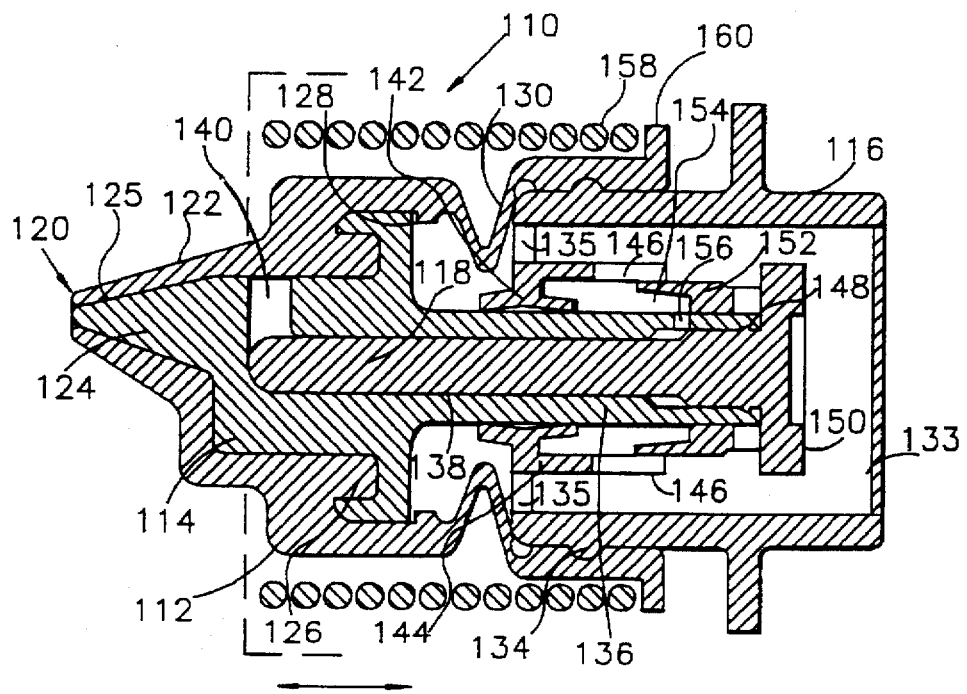
FIG. 4 is a cross-sectional view of the apparatus of FIG. 3 illustrated in an actuated position for releasing a dose of medicament through the nozzle.

In FIGS. 3 and 4 another apparatus embodying the present invention is indicated generally by the reference numeral 110. The apparatus 110 is similar to the apparatus 10 described above, and therefore like reference numerals preceded by the numeral 1 are used to indicate like elements. The apparatus 110 includes an outer body 112, an inner body 114 fitted within the outer body 112, and a piston body 116 coupled to the outer body 112. The outer body 112 and inner body 114 define a nozzle 120 for releasing drops into a user's eye upon movement of the piston body 116 relative to the outer body 112, as indicated by the arrows in FIGS. 3 and 4. The nozzle 120 is the same as the nozzle 20.

The outer body 112 defines an outer nozzle portion 122 which receives an inner nozzle portion 124 of the inner body 114. The interface of the outer nozzle portion 122 and the inner nozzle portion 124 defines a seam 125 which is normally closed (i.e., the inner and outer nozzle portions are abutting one another as shown in the drawings), but can be opened by the flow of medicament of sufficient pressure into the seam to release the medicament through the nozzle 120. As with the nozzle 20 described above, the outer body 112 is preferably molded from a relatively flexible plastic material in comparison to the inner body 114. Thus, the outer nozzle portion 122 can be flexed relative to the inner nozzle portion 124 to open the seam 125 to release the medicament through the nozzle 120.

The outer body 112 includes an annular flange 126 which fits within a corresponding recess in the inner body 114, as shown in FIGS. 3 and 4. The inner body 114, on the other hand, includes an annular lip 128 which retains the inner body 114 within the outer body 112. The inner body 114 is therefore pressed into the outer body 112 and coupled to the outer body by guiding the flange 126 into the corresponding recess and snapping the outer body 114 within the lip 128 of the inner body.

The outer body 112 further includes a bellows 130 and a flange 132 coupled to the piston body 116. A medicament chamber 133 is thus defined within the outer body 112 and within the piston body 116, as shown in FIGS. 3 and 4. The piston body 116 includes an aperture 135 to permit the medicament within the chamber 133 to flow between the interior of the outer body 112 and the interior of the piston body 116. The piston body 116 includes a lobe 134 which is snapped into a corresponding recess in the flange 132 to couple the piston body to the outer body 112, as shown in FIGS. 3 and 4. As will be recognized by those skilled in the art, however, the outer body 112 and piston body 116 can equally be molded as an integral body to further prevent any leaks within the apparatus due to changes in the ambient pressure or temperature, for example.

The outer end of the piston body 116 is sealed in a manner known to those skilled in the art to retain the medicament within the medicament chamber 133. The other end of the piston body 116 can also be coupled to another container, for example, for pre-packaging the medicament in a manner known to those skilled in the art. The bellows 130 is adapted to flex inwardly to permit the piston body 116 to move relative to the outer body 112 to release medicament stored within the medicament chamber 133 through the nozzle 120.

The inner body 114 includes a first substantially cylindrical wall 136 essentially defining a hollow shaft projecting in the axial direction of the apparatus 110 and surrounding a rod member 118, as shown in FIGS. 3 and 4. A first channel 138 is defined between the rod member 118 and the first cylindrical wall 136, and a second channel 140 extends between the first channel 138 and the seam 125.

The piston body 116 includes a bushing 142 which receives the first cylindrical wall 136, and thus guides the piston body 116 as it is moved along the first cylindrical wall. As shown in FIGS. 3 and 4, the interior surface of the bushing 142 defines a generally concave profile for engaging the cylindrical wall 136 in a fluid-tight manner, and thus substantially prevents the flow of medicament between the bushing 142 and the cylindrical wall 136 upon moving the piston body 116 to release medicament.

The piston body 116 further includes a second cylindrical wall 144 which is substantially concentric with the first cylindrical wall 136, and defines at least two slots 146 coupling the interior of the second cylindrical wall 144 in fluid communication with the medicament chamber 133. As shown in FIGS. 3 and 4, the rod member 118 is coupled to the first cylindrical wall 136 by means of a lobe 148 which snaps into a corresponding recess in the first cylindrical wall. A flange 150 on the end of the rod member 118 rests against the top surfaces of the first cylindrical wall 136 and the second cylindrical wall 144 to prevent the piston body 116 from being moved any further away from the nozzle 120.

As shown in FIGS. 3 and 4, a flange member 152 is coupled to the end of the first cylindrical wall 136 and tapers outwardly so that its free end engages the interior surface of the second cylindrical wall 144. The second cylindrical wall 144 and the flange member 152 thus define a drop cavity 154 for holding medicament for release into the eye. The drop cavity 154 is preferably dimensioned to cause less than about 30 microliters of medicament to be released each time the apparatus 110 is actuated. For many medicaments, the drop cavity 154 is preferably dimensioned to release approximately 15 to 20 microliters of medicament each time the apparatus is actuated. This volume of medicament is only exemplary, however, and can be changed as desired by changing the volume of the drop cavity 154, for example.

The free end of the flange member 152 is dimensioned so that it engages the interior surface of the second cylindrical wall 144 in order to substantially prevent the flow of medicament between the second cylindrical wall 144 and the flange member 152 upon movement of the piston body 116, as indicated by the arrows in FIGS. 3 and 4. The first cylindrical wall 136 defines an aperture 156 extending between the first channel 138 and the drop cavity 154 to permit the flow of medicament from the drop cavity 154, through the first channel 138 and second channel 140, for release through the nozzle 120 into the eye.

The apparatus 110 is preferably employed for use in a device such as the ocular treatment apparatus shown and described in U.S. Pat. No. 4,981,479. The modifications that are necessary in order to use the apparatus 110 with such an ocular treatment apparatus will be known to those skilled in the pertinent art, particularly in view of the teachings of U.S. Pat. No. 4,981,479. The outer body 112 is seated against a surface of the ocular treatment apparatus, as indicated by phantom lines in FIGS. 3 and 4, in order to maintain the outer body 112 in a stationary position. A coil spring 158 is preferably seated between the surface of the ocular treatment apparatus and an annular lip 160 on the flange 132. The coil spring 158 is provided to drive the piston body 116 to return to its normal position for dispensing medicament.

In the operation of the apparatus 110, the apparatus is normally oriented in the position shown in FIG. 3 (i.e., the bellows 130 is in a relaxed state). The apparatus 110 is actuated to release medicament through the nozzle 120 by depressing the piston body 116 toward the outer body 112, as shown in FIG. 4. As a result, the bellows 130 is depressed inwardly and the bushing 142 is moved down toward the nozzle 120, causing a suction to develop within the drop cavity 154, the first channel 138 and the second channel 140. The suction facilitates the flow of medicament from the medicament chamber 133 through the slots 146 to fill the drop cavity 154 and the first and second channels 138 and 140. Once the piston body 116 reaches the end of its downward stroke, as shown in FIG. 4, the piston body is released, thus permitting the coil spring 158 to drive the piston body 116 in the opposite direction away from the nozzle 120.

As a result, the bushing 142 slides back along the first cylindrical wall 136 toward the flange member 152. Then, at about the point that the bottom of each slot 146 passes over the end of the flange portion 152, the medicament in the drop cavity 154 is forced by the bushing 142 through the aperture 156 and into the first channel 138. The pressurized medicament flows through the second channel 140, into the seam 125, and out through the tip of the nozzle 120 for release into the eye. The pressure caused by the force of the coil spring 158 driving the bushing 142 is sufficient to cause the medicament to open the seam 125 so that the complete dose of medicament is released into the eye. Then, once the medicament is released, the seam 125 returns to its normally closed position to substantially prevent any medicament that is exposed to air from flowing back into the apparatus. The apparatus 110 is then ready to be actuated again to release another dose of medicament.

As will be recognized by those skilled in the art, one advantage of the apparatus of the present invention is that a substantially predetermined volume of medicament can be released into an eye each time the apparatus is actuated. The predetermined volume released can be controlled by controlling the volume of the drop cavity, for example. Another advantage of the apparatus of the present invention is that once a dose of medicament is released, the seam of the nozzle closes, and thus substantially prevents medicament which has been exposed to air or foreign particles from passing through the nozzle and into the apparatus, which can, in some instances, contaminate the remainder of the medicament in the apparatus. This advantage is particularly important when storing multiple-dose quantities of preservative-free formulations of medicament or other substances within the apparatus.

Another advantage of the apparatus 110 is that the pumping mechanism, which includes the first cylindrical wall 136 and the actuating member 142, is contained entirely within the medicament chamber 133, and thus further prevents any contamination of the remaining medicament within the apparatus when actuating the pumping mechanism. Another advantage of the apparatus 110 is that the medicament is dispensed upon the release of the piston body 116. In this way, the same quantity of medicament is released each time the apparatus is actuated, because it is the force of the coil spring 158 which causes the medicament to be dispensed from the apparatus. Thus, the apparatus 110 can be used to reliably dispense medicament, regardless of whether a user's hand shakes, or if there are variations in the speed of the downward stroke of the piston body 116.

I claim:

1. An apparatus for applying a certain predetermined dosage of a fluid into an eye, comprising:

a container holding a volume of fluid;

a first dosage cavity forming member and a second dosage cavity forming member, the second member being movable between: a first position, in which the first member and the second member together define a cavity which is in fluid communication with the container; a second position, in which the first member and the second member together define a cavity having a certain predetermined volume and in which the cavity is not in fluid communication with the container; and a third position in which the volume of the cavity is less than the volume of the cavity in the second position and in which the cavity is not in fluid communication with the container;

a means for biasing the second dosage cavity forming member to the third position; and a nozzle which is in fluid communication with the cavity, wherein a dosage of fluid in the cavity is forced through the nozzle and out of the apparatus upon movement of the second member from the first position or from the second position to the third position under the action of the biasing means, and wherein the second member is selectively movable from the third position back to the first position to draw fluid from the container into the cavity after each dosage of fluid is forced through the nozzle out of the apparatus.

2. The apparatus according to claim 1, wherein a dosage of fluid which is substantially equal to the volume of the cavity in the second position of the second member is forced through the nozzle upon movement of the second member from the second position to the third position under the action of the biasing means.

3. The apparatus according to claim 2, wherein the second member is a hollow member which includes a wall.

4. The apparatus according to claim 3, wherein the wall of the second cavity forming member has an inner surface and wherein the first cavity forming member has a wall which engages said inner surface in sliding, sealing contact as the second member is moved from the second position to the third position.

5. The apparatus according to claim 2, wherein the volume of the dosage cavity in the second position of the second cavity forming member is less than 30 microliters.

6. The apparatus according to claim 1, wherein the second member is a hollow member which includes a wall.

7. The apparatus according to claim 6, wherein the wall of the second cavity forming member has an inner surface and wherein the first cavity forming member has a wall which engages said inner surface in sliding, sealing contact as the second member is moved from the second position to the third position.

8. The apparatus according to claim 7, wherein the wall of the first cavity forming member includes a flexible rim which makes sliding, sealing contact with the inner surface of the wall of the second cavity forming member as the second member is moved from the second position to the third position.

9. The apparatus according to claim 7, wherein a portion of the wall of the second cavity forming member defines a slot therethrough for placing the cavity in fluid communication with the container in the first position of the second member.

10. The apparatus according to claim 1, wherein the biasing means is a spring.

11. The apparatus according to claim 1, further comprising a channel which couples the cavity to the nozzle to place the cavity in fluid communication with the nozzle.

12. The apparatus according to claim 1 wherein the fluid is an eye medication.

13. The apparatus according to claim 1, wherein the difference in volume between the volume of the dosage cavity in the second position of the second cavity forming member and the volume of the cavity in the third position of the second member is less than 30 microliters.

14. An apparatus for applying a certain predetermined dosage of a fluid into an eye, comprising:

a container holding a volume of fluid;

a first dosage cavity forming member and a second dosage cavity forming member, the second member being movable between: a first position, in which the first member and the second member together define a cavity which is in fluid communication with the container; a second position, in which the first member and the second member together define a cavity having a certain predetermined volume and in which the cavity is not in fluid communication with the container; and a third position in which the volume of the cavity is less than the volume of the cavity in the second position and in which the cavity is not in fluid communication with the container;

a means for biasing the second dosage cavity forming member to the third position; and a nozzle which is in fluid communication with the cavity, wherein a dosage of fluid in the cavity is forced through the nozzle and out of the apparatus upon movement of the second member from the first position or from the second position to the third position under the action of the biasing means, and wherein the second member is selectively movable from the third position back to the first position to draw fluid from the container into the cavity after each dosage of fluid is forced through the nozzle out of the apparatus;

the nozzle including an inner nozzle forming member and an outer nozzle forming member which define an interface at an area of contact between them, the area of contact preventing passage of fluid through the nozzle, and wherein the area of contact is at least partially severed by fluid forced out of the cavity and into the nozzle as the second cavity forming member is forced from the second position to the third position by the biasing means, the area of contact being restored upon expulsion of the fluid from the nozzle.

15. The apparatus according to claim 14, wherein a dosage of fluid which is substantially equal to the volume of the cavity in the second position of the second member is forced through the nozzle upon movement of the second member from the second position to the third position under the action of the biasing means.

16. The apparatus according to claim 15, wherein the second member is a hollow member which includes a wall.

17. The apparatus according to claim 16, wherein the wall of the second cavity forming member has an inner surface and wherein the first cavity forming member has a wall which engages said inner surface in sliding, sealing contact as the second member is moved from the second position to the third position.

18. The apparatus according to claim 15, wherein the volume of the dosage cavity in the second position of the second cavity forming member is less than 30 microliters.

19. The apparatus according to claim 14, wherein the second member is a hollow member which includes a wall.

20. The apparatus according to claim 19, wherein the wall of the second cavity forming member has an inner surface and wherein the first cavity forming member has a wall which engages said inner surface in sliding, sealing contact as the second member is moved from the second position to the third position.

21. The apparatus according to claim 20, wherein the wall of the first cavity forming member includes a flexible rim which makes sliding, sealing contact with the inner surface of the wall of the second cavity forming member as the second member is moved from the second position to the third position.

22. The apparatus according to claim 20, wherein a portion of the wall of the second cavity forming member defines a slot therethrough for placing the cavity in fluid communication with the container in the first position of the second member.

23. The apparatus according to claim 14, wherein the outer nozzle member is more flexible than the inner nozzle member for facilitating severing of the area of contact in response to a flow of fluid from the cavity upon forced movement of the second member from the second position to the third position under the action of the biasing means.

24. The apparatus according to claim 14, wherein the biasing means is a spring.

25. The apparatus according to claim 14, further comprising a channel which couples the cavity to the nozzle to place the cavity in fluid communication with the nozzle.

26. The apparatus according to claim 14 wherein the fluid is an eye medication.

27. The apparatus according to claim 14, wherein the difference in volume between the volume of the dosage cavity in the second position of the second cavity forming member and the volume of the cavity in the third position of the second member is less than 30 microliters.

* * * * *